(12) United States Patent
Fukumoto et al.

(10) Patent No.: US 8,350,232 B2
(45) Date of Patent: Jan. 8, 2013

(54) MICROPARTICLE ANALYSIS DEVICE AND MICROPARTICLE ANALYSIS METHOD

(75) Inventors: Atsushi Fukumoto, Kanagawa (JP); Mitsuru Toishi, Kanagawa (JP)

(73) Assignee: Sony Corporation, Tokyo (JP)

( * ) Notice: Subject to any disclaimer, the term of this patent is extended or adjusted under 35 U.S.C. 154(b) by 34 days.

(21) Appl. No.: 13/017,554

(22) Filed: Jan. 31, 2011

(65) Prior Publication Data
US 2011/0192991 A1 Aug. 11, 2011

(30) Foreign Application Priority Data
Feb. 5, 2010 (JP) ................. P2010-023720

(51) Int. Cl.
*G01N 21/64* (2006.01)
(52) U.S. Cl. .................................... 250/459.1
(58) Field of Classification Search ............. 250/459.1, 250/458.1
See application file for complete search history.

(56) References Cited

U.S. PATENT DOCUMENTS 4,573,796 A * 3/1986 Martin et al. ............... 356/318
5,946,090 A * 8/1999 Tashiro et al. ............. 356/326
7,417,211 B2 * 8/2008 Nakata et al. ............. 250/201.3
2008/0180782 A1 * 7/2008 Kump et al. ............... 359/285
2009/0122825 A1 * 5/2009 Ershov et al. ............... 372/57

FOREIGN PATENT DOCUMENTS
JP 2007-46947 2/2007

OTHER PUBLICATIONS

Adams et al., "A high-speed multispectral spinning-disk confocal microscope system for fluorescent speckle microscopy of living cells," 2002, Methods, vol. 29, pp. 29-41.*

* cited by examiner

*Primary Examiner* — Kiho Kim
(74) *Attorney, Agent, or Firm* — K&L Gates LLP

(57) ABSTRACT

Disclosed herein is a microparticle analysis device including: a light source configured to irradiate a microparticle with light; an acousto-optic modulator configured to diffract fluorescence generated from the microparticle due to the light irradiation; a slit configured to allow transmission of only diffracted light in a diffraction center wavelength region among diffracted light beams from the acousto-optic modulator; and a detector configured to detect the diffracted light in the diffraction center wavelength region transmitted through the slit.

2 Claims, 6 Drawing Sheets

MICROPARTICLE ANALYSIS DEVICE AND MICROPARTICLE ANALYSIS METHOD

CROSS REFERENCES TO RELATED APPLICATIONS

The present application claims priority to Japanese Priority Patent Application JP 2010-023720 filed in the Japan Patent Office on Feb. 5, 2010, the entire content of which is hereby incorporated by reference.

BACKGROUND

The present invention relates to microparticle analysis devices and microparticle analysis methods. More specifically, the invention relates to a microparticle analysis device and so forth to optically analyze characteristics of microparticles such as cells and microbeads.

As a related art, microparticle analysis devices are used in which microparticles flowing in a flow cell or a flow path formed on a microchip are irradiated with light and scattered light from the microparticles and fluorescence generated from the microparticles themselves or a fluorescent substance given to the microparticles as a labeling substance are detected to measure optical characteristics of the microparticles. In the microparticle analysis devices, fractional collection of a population (group) determined to be one satisfying a predetermined condition among the microparticles as a result of the measurement of the optical characteristics is also performed. Among the microparticle analysis devices, particularly a device to measure optical characteristics of cells as the microparticles and perform fractional collection of a cell population satisfying a predetermined condition is called e.g. a flow cytometer or a cell sorter.

For example, Japanese Patent Laid-open No. 2007-46947 (hereinafter, Patent Document 1) discloses "a flow cytometer comprising a plurality of light sources to radiate a plurality of excitation light beams having wavelengths different from each other with a predetermined cycle and phases different from each other, and an optical guide member to guide the plurality of excitation light beams onto the same incident light path and condense the light beams on dyed particles." This flow cytometer includes the plurality of light sources to radiate a plurality of excitation light beams having wavelengths different from each other, the optical guide member to guide the plurality of excitation light beams onto the same incident light path and condense the light beams on dyed particles, and a plurality of fluorescence detectors to detect fluorescence generated due to excitation of the particles by each of the plurality of excitation light beams and output a fluorescence signal (see claims 1 and 3 and FIGS. 1 and 3 in Patent Document 1).

In the related-art microparticle analysis device like that disclosed in Patent Document 1, fluorescence generated from microparticles or a fluorescent substance given to the microparticles as a labeling substance is spatially divided into fluorescence in plural wavelength regions by using a wavelength filter and a dichroic mirror, and the divided fluorescence in the respective wavelength regions is detected by individual detectors.

FIG. 6 schematically shows the optical path for the fluorescence detection in the related-art microparticle analysis device. Light (excitation light) from a light source indicated by reference numeral 11 in the diagram passes through a collimator lens 12 and a mirror 13 to be irradiated on microparticles P flowing in a flow cell or a flow path formed on a microchip by a condenser lens 14. In the diagram, arrowhead F indicates the flow sending direction of the sheath flow in the flow cell or the like.

The fluorescence generated from the microparticles P or a fluorescent substance given to the microparticles P as a labeling substance due to the irradiation with the excitation light passes through a condenser lens 15 and is transmitted through plural wavelength filters 161 to 164 sequentially. At this time, fluorescence in a predetermined wavelength region is dispersed by each wavelength filter. The fluorescence dispersed by the respective wavelength filters is detected by detectors 171 to 174 provided for each of the wavelength filters and converted to an electrical signal. FIG. 7 shows one example of the wavelength regions of the fluorescence detected by the detectors 171 to 174. This example corresponds to the case in which fluorescence in a wavelength region $\lambda 1$ is detected by the detector 171 and fluorescence in wavelength regions $\lambda 2$ to $\lambda 4$ is detected by the detectors 172 to 174, respectively.

SUMMARY

In the related-art microparticle analysis device including the fluorescence detection path like that shown in FIG. 6, the plural detectors are necessary to individually detect the spatially-divided fluorescence in the respective wavelength regions. Therefore, the related-art device has problems of large device size and high device manufacturing cost.

There is a need for the present invention to provide, as a microparticle analysis device, a device capable of separating fluorescence generated from microparticles or a fluorescent substance given to the microparticles as a labeling substance into plural wavelength regions and individually detecting the separated fluorescence without provision of plural detectors.

According to a mode of the present invention, there is provided a microparticle analysis device including a light source configured to irradiate a microparticle with light and an acousto-optic modulator configured to diffract fluorescence generated from the microparticle due to the light irradiation. The microparticle analysis device further includes a slit configured to allow transmission of only diffracted light in a diffraction center wavelength region among diffracted light beams from the acousto-optic modulator and a detector configured to detect the diffracted light in the diffraction center wavelength region transmitted through the slit.

According to another mode of the present invention, there is provided a microparticle analysis method including the steps of diffracting fluorescence generated from a microparticle due to light irradiation by an acousto-optic modulator that provides a diffraction center wavelength region made to correspond with a detected-fluorescence wavelength region, making diffracted light from the acousto-optic modulator be transmitted through a slit that allows transmission of only diffracted light in the diffraction center wavelength region, and detecting the diffracted light in the diffraction center wavelength region transmitted through the slit.

In the modes of the present invention, the "microparticle" broadly encompasses biologically-relevant microparticles such as cells, microorganisms, and liposomes, synthetic particles such as latex particles, gel particles, and industrial particles, and so forth.

The biologically-relevant microparticle encompasses chromosomes, liposomes, mitochondria, organelles, etc. configuring various kinds of cells. The cell as the subject encompasses animal cells (hemocyte cell, etc.) and plant cells. The microorganism encompasses bacteria such as coliforms, viruses such as tobacco mosaic viruses, fungi such as yeast fungi, and so forth. Moreover, in the biologically-relevant microparticle, biologically-relevant polymers such as nucleic acids, proteins, and complexes of them can also be encompassed.

The industrial particle may be e.g. an organic or inorganic polymer material or a metal. The organic polymer material encompasses polystyrene, styrene divinylbenzene, polymethylmethacrylate, etc. The inorganic polymer material encompasses glass, silica, magnetic materials, etc. The metal encompasses gold colloids, aluminum, etc. The shape of these microparticles is generally spherical. However, the shape may be non-spherical, and the size, the mass, etc. are also not particularly limited.

The modes of the present invention provide, as a microparticle analysis device, a device capable of separating fluorescence generated from microparticles or a fluorescent substance given to the microparticles as a labeling substance into plural wavelength regions and individually detecting the separated fluorescence without provision of plural detectors.

Additional features and advantages are described herein, and will be apparent from the following Detailed Description and the figures.

DETAILED DESCRIPTION

Embodiments of the present application will be described below in detail with reference to the drawings.

A preferred mode for carrying out the present invention will be described below with reference to the drawings. It should be noted that an embodiment to be described below shows one example of representative embodiments and the scope of the present invention is not narrowly interpreted due to this embodiment.

Figure 1:
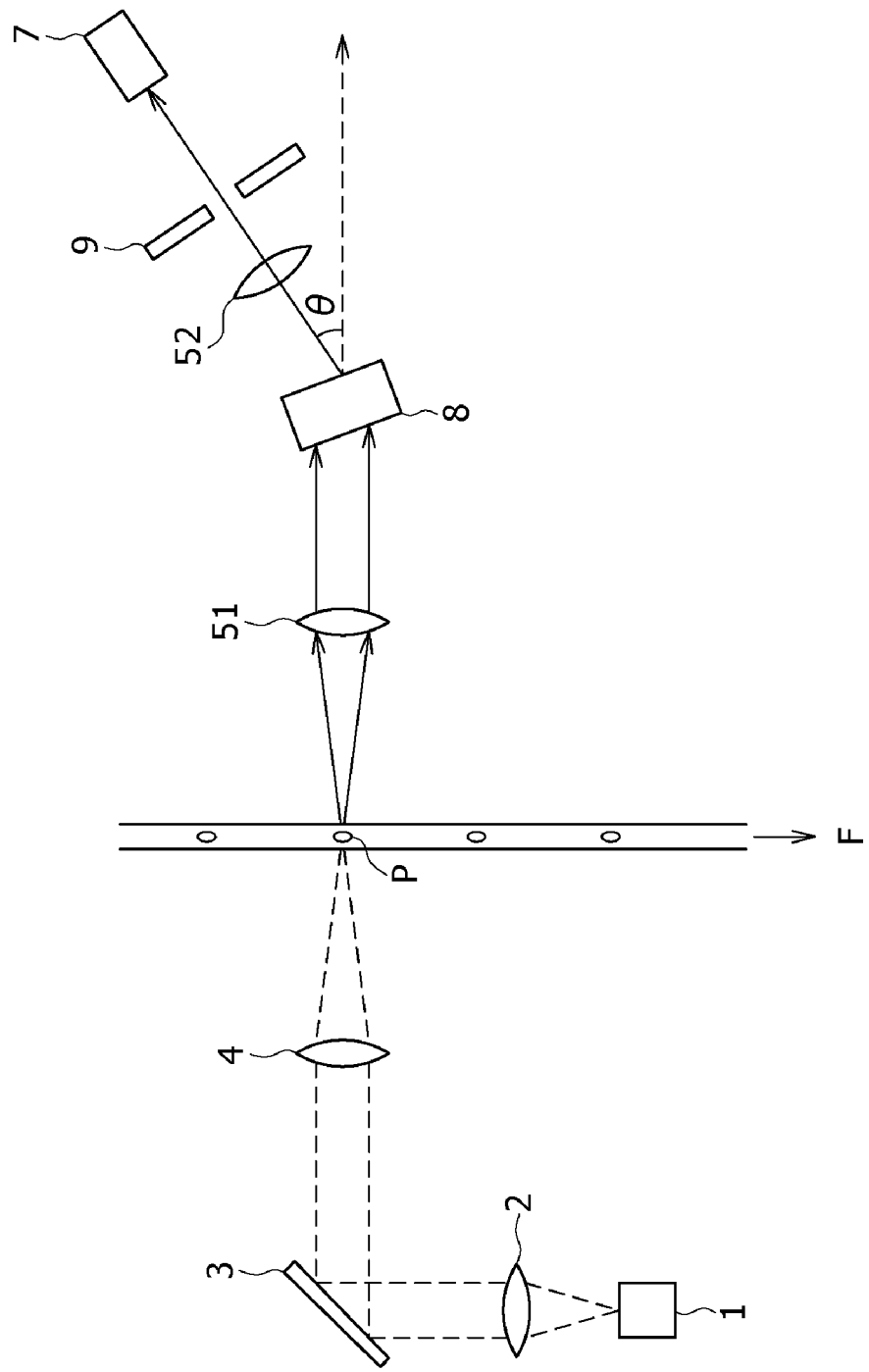
FIG. 1 is a schematic diagram for explaining a fluorescence detection path of a microparticle analysis device according to an embodiment.

FIG. 1 schematically shows the fluorescence detection path of a microparticle analysis device according to the embodiment.

Light (excitation light) from a light source indicated by reference numeral 1 in the diagram is irradiated on microparticles P flowing in a flow cell or a flow path formed on a microchip by an irradiation system composed of a collimator lens 2, a mirror 3, a condenser lens 4, and so forth. In the diagram, arrowhead F indicates the flow sending direction of the sheath flow in the flow cell or the like. The light irradiation system to irradiate the microparticles P with the light may have a configuration similar to that in a publicly-known microparticle analysis device and is not limited to the configuration shown in the diagram.

Fluorescence generated from the microparticles or a fluorescent substance given to the microparticles as a labeling substance due to the irradiation with the excitation light passes through a condenser lens 51 and is guided to a detection system composed of an acousto-optic modulator 8, a condenser lens 52, a slit 9, a detector 7, and so forth. Furthermore, the detection system in the microparticle analysis device according to the embodiment includes a detector for detecting scattered light from the microparticles and a mirror, a filter, etc. for guiding the scattered light to the detector, configured similarly to a publicly-known microparticle analysis device (diagrammatic representation thereof is omitted).

The fluorescence incident on the acousto-optic modulator 8 is diffracted by a Bragg diffraction grating in the acousto-optic modulator 8 and condensed, by the condenser lens 52, on the slit 9 provided at the focal plane of the condenser lens 52. The fluorescence of the respective wavelengths diffracted by the acousto-optic modulator 8 is disposed on the surface of the slit 9 in such a manner that the light of the diffraction center wavelength having the highest diffraction efficiency depending on the pitch of the diffraction grating is at the center. In FIG. 1, sign θ indicates the diffraction angle of the light of the diffraction center wavelength.

Figure 2:
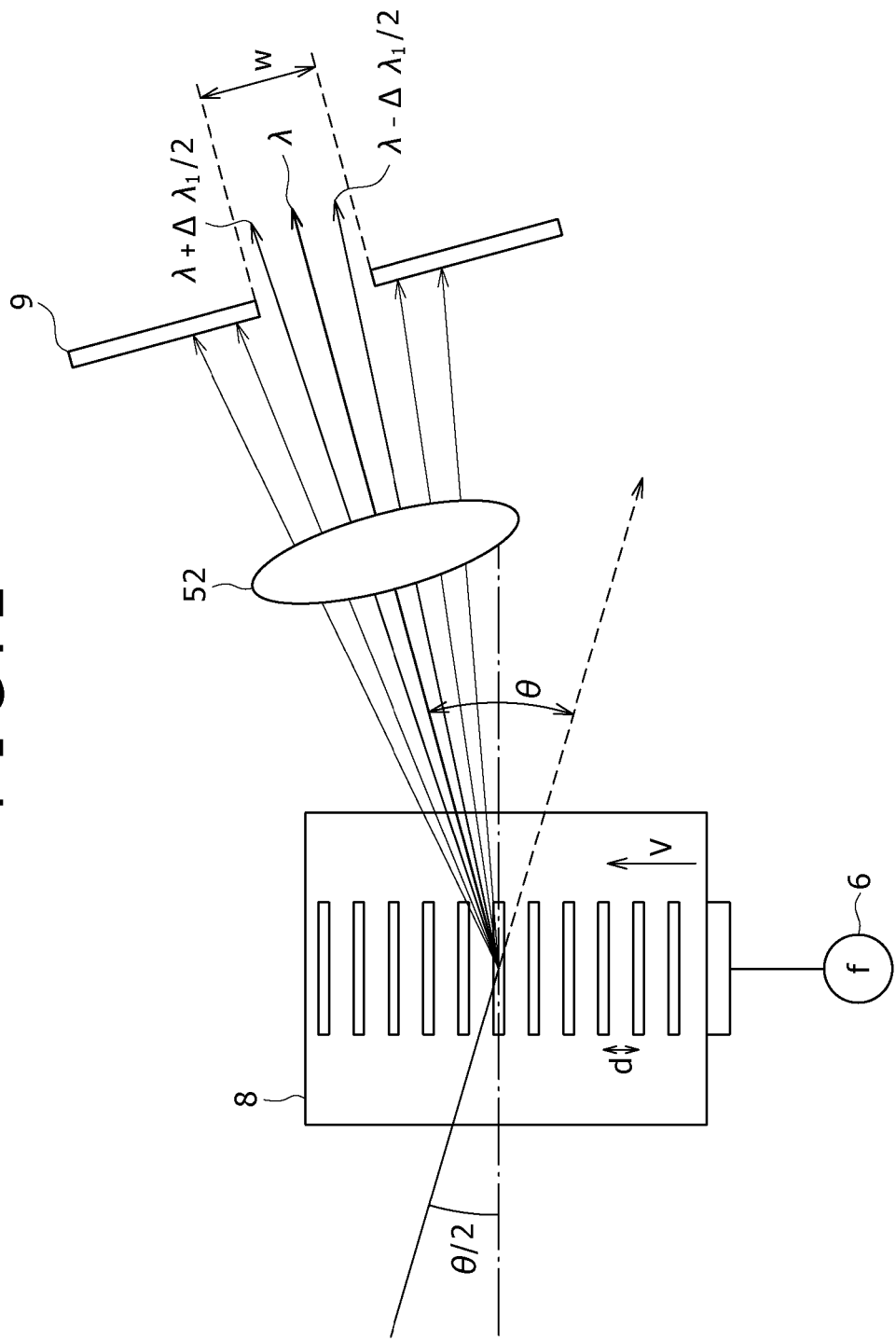
FIG. 2 is a schematic diagram for explaining fluorescence beams of the respective wavelengths diffracted by an acousto-optic modulator and disposed on the surface of a slit.

FIG. 2 schematically shows the fluorescence of the respective wavelengths diffracted by the acousto-optic modulator 8 and disposed on the surface of the slit 9.

Inside the crystal of the acousto-optic modulator 8, by an acoustic wave with a frequency f and an acoustic wave velocity v applied by a frequency controller 6, the diffraction grating whose pitch d is v/f is formed. If the incidence angle of the fluorescence incident on the diffraction grating is defined as θ/2, the diffraction center wavelength λ having the highest diffraction efficiency in the direction of the diffraction angle θ is represented by Equation (1) shown below based on the diffraction formula of the Bragg condition.

[Expression 1]

$$2d \sin(\theta/2) = m\lambda \qquad \text{Equation (1)}$$

(in this equation, m denotes the diffraction order)

In the slit 9, a rectangular aperture is formed. This rectangular aperture allows transmission of only fluorescence in a wavelength region with a wavelength width $\Delta\lambda_1$, including the diffraction center wavelength λ, among the fluorescence beams of the respective wavelengths disposed on the surface of the slit 9 in such a manner that the light of the diffraction center wavelength λ is at the center. In the diagram, sign w indicates the aperture width of the slit 9.

Due to this aperture, the slit 9 transmits, to the detector 7 (see FIG. 1), only the fluorescence in the diffraction center wavelength region from a wavelength of $\lambda - \Delta\lambda_1/2$ to a wavelength of $\lambda + \Delta\lambda_1/2$ among the fluorescence beams diffracted by the acousto-optic modulator 8. At this time, the lowering of the diffraction efficiency of light involving a deviation from the diffraction center wavelength λ can be minimized by decreasing the incidence angle θ/2 of the fluorescence incident on the diffraction grating.

The detector 7 detects the fluorescence in the diffraction center wavelength region transmitted through the aperture of the slit 9 and converts the fluorescence to an electrical signal. The detector 7 and the detector (not shown) for detecting scattered light may have a configuration similar to that in a publicly-known microparticle analysis device. For example, a photo multiplier tube (PMT) or an area imaging element such as a CCD or a CMOS element is employed as the detectors. The electrical signal converted by the detector 7 and the detector for detecting scattered light is used for measurement of optical characteristics of the microparticle P. The parameters for the optical characteristic measurement are the same as those used in a publicly-known microparticle analysis device. Specifically, for example, forward-scattered light is employed as the parameter in determination as to the size of the microparticle P. In addition, side-scattered light is employed in determination as to the structure, and fluorescence or the like is employed in determination as to the presence or absence of a fluorescent substance given to the microparticles P as a labeling substance.

If it is assumed that, in the above Equation (1), the diffraction order m is 1 and the incidence angle (θ/2) of fluorescence that is generated from the microparticle P and incident on the diffraction grating is sufficiently small, the diffraction center wavelength λ having the highest diffraction efficiency in the direction of the diffraction angle θ is represented by Equation (2) shown below.

[Expression 2]

$$\theta = \lambda/d = \left(\frac{f \cdot \lambda}{v}\right) \quad \text{Equation (2)}$$

In Equation (2), the acoustic wave velocity v is constant due to the dependence of the acousto-optic modulator 8 on the crystal. Therefore, the diffraction center wavelength λ of fluorescence diffracted in the direction of the diffraction angle θ can be controlled by changing the frequency f of the acoustic wave applied to the acousto-optic modulator 8 by the frequency controller 6.

Figure 3:
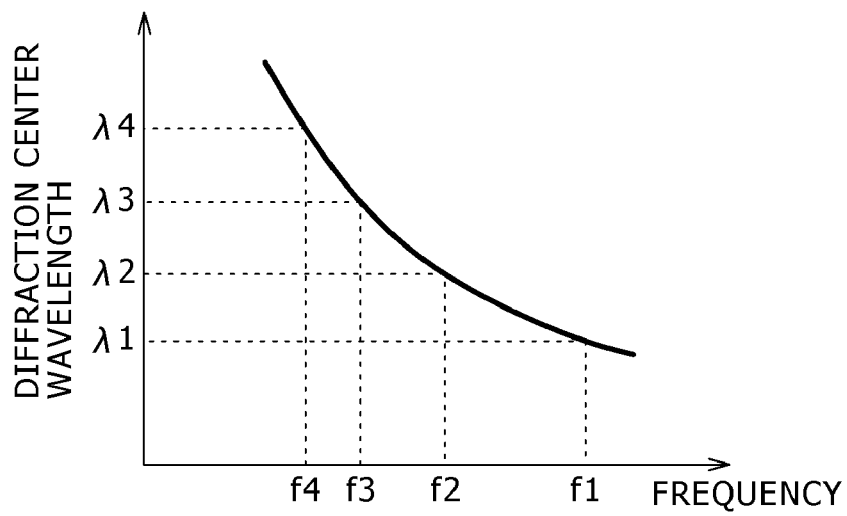
FIG. 3 is a schematic diagram for explaining the relationship between the frequency f of an acoustic wave applied to the acousto-optic modulator by a frequency controller and the diffraction center wavelength λ of fluorescence diffracted in the direction of a diffraction angle θ.

FIG. 3 shows the relationship between the frequency f of the acoustic wave applied to the acousto-optic modulator 8 by the frequency controller 6 and the diffraction center wavelength λ of fluorescence diffracted in the direction of the diffraction angle θ.

Suppose that, as shown in the diagram, the diffraction center wavelength having the highest diffraction efficiency in the direction of the diffraction angle θ is λ1 when an acoustic wave of a frequency f1 is applied to the acousto-optic modulator 8 by the frequency controller 6. In this case, for example, the diffraction center wavelength changes to λ2 if the frequency of the acoustic wave applied to the acousto-optic modulator 8 is changed to f2. Similarly, the diffraction center wavelength changes to λ3 and λ4 by change of the frequency of the acoustic wave applied to the acousto-optic modulator 8 to f3 and f4.

In this manner, the diffraction center wavelength λ of fluorescence diffracted in the direction of the diffraction angle θ can be arbitrarily controlled based on the frequency f of the acoustic wave applied to the acousto-optic modulator 8 by the frequency controller 6. Furthermore, the diffraction direction (angle θ) of the diffraction center wavelength λ is always kept constant due to the Bragg condition. Therefore, by changing the frequency f of the acoustic wave applied to the acousto-optic modulator 8 by the frequency controller 6, the wavelength region of fluorescence transmitted through the aperture of the slit 9 (diffracted light in the diffraction center wavelength region from a wavelength of λ−Δλ1/2 to a wavelength of λ+Δλ1/2), among the fluorescence beams diffracted by the acousto-optic modulator 8, can be arbitrarily controlled. Due to this feature, the wavelength region of the fluorescence detected by the detector 7 can be set to an arbitrary wavelength region (detected-fluorescence wavelength region).

Furthermore, the wavelength width Δλ1 of the fluorescence detected by the detector 7 can be arbitrarily set by accordingly changing the aperture width w of the slit 9 (see FIG. 2). Specifically, if the aperture width w of the slit 9 is widened, fluorescence in a wider wavelength band can be detected by the detector 7. In contrast, if the aperture width w is narrowed, fluorescence in a narrower wavelength band is detected. It is preferable that the aperture width w of the slit 9 be set to the width considered as the most effective width for fluorescence in all detected-fluorescence wavelength regions.

Figure 4:
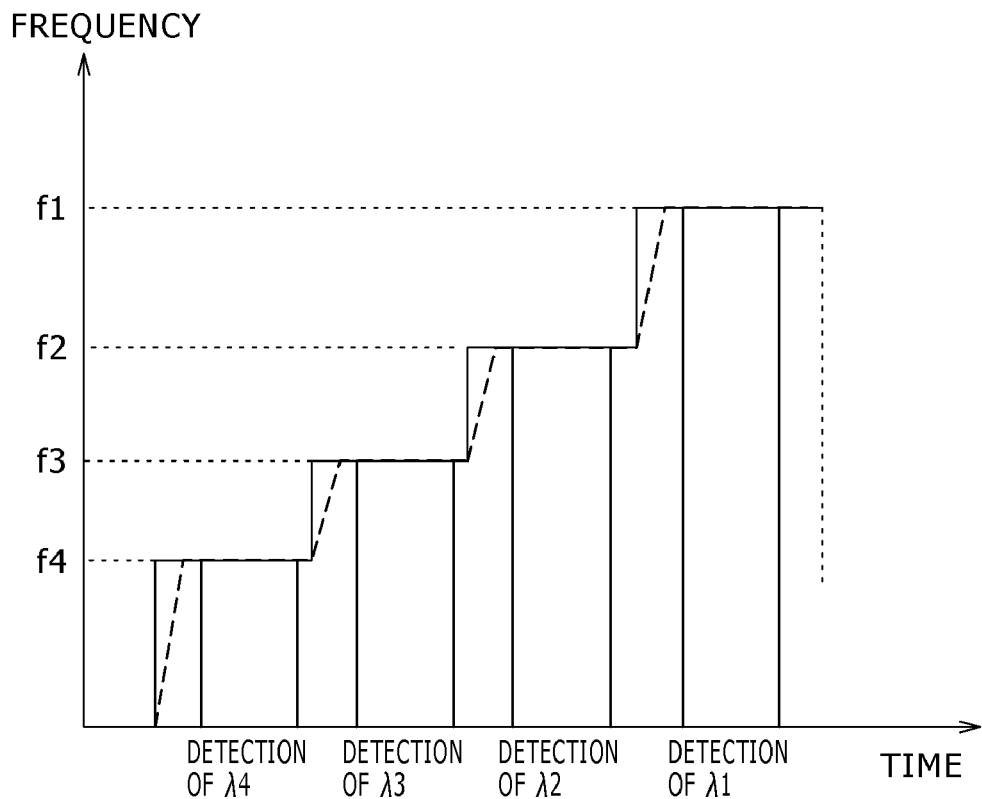
FIG. 4 is a schematic diagram for explaining the relationship between the frequency f of the acoustic wave applied to the acousto-optic modulator by the frequency controller and the wavelength region of the fluorescence detected by a detector.

FIG. 4 shows the relationship between the frequency f of the acoustic wave applied to the acousto-optic modulator 8 by the frequency controller 6 and the wavelength region of the fluorescence detected by the detector 7. In the diagram, the full line indicates change in the frequency f of the acoustic wave applied to the acousto-optic modulator 8 by the frequency controller 6. The dotted line indicates change in the wavelength region of the fluorescence detected by the detector 7. The bars indicate the times of detection of fluorescence in the respective wavelength regions by the detector 7.

As shown in the diagram, when an acoustic wave of the frequency f1 is applied to the acousto-optic modulator 8 by the frequency controller 6, the diffraction center wavelength having the highest diffraction efficiency in the direction of the diffraction angle θ is λ1, so that fluorescence in the wavelength width Δλ1 around λ1 as the center wavelength is detected by the detector 7. When the frequency of the acoustic wave applied to the acousto-optic modulator 8 is changed to f2, the diffraction center wavelength changes to λ2. Thus, the fluorescence detected by the detector 7 changes to fluorescence in the wavelength width Δλ1 around λ2 as the center wavelength. At this time, the time when the fluorescence in the wavelength width Δλ1 around λ2 as the center wavelength is detected by the detector 7 delays by the time until stabilization of the diffraction grating in the acousto-optic modulator 8 after the switching of the applied acoustic wave.

Similarly, by discontinuously changing the frequency of the acoustic wave applied to the acousto-optic modulator 8 to f3 and f4, the fluorescence detected by the detector 7 is changed to the fluorescence in the wavelength width Δλ1 around λ3 and λ4, respectively, as the center wavelength sequentially.

In this manner, the wavelength region of the fluorescence detected by the detector 7 can be arbitrarily controlled based on the frequency f of the acoustic wave applied to the acousto-optic modulator 8 by the frequency controller 6. Therefore, by discontinuously changing the frequency f of the acoustic wave applied to the acousto-optic modulator 8 by the frequency controller 6 depending on the arbitrary detected-fluorescence wavelength region as the detection target, fluorescence in plural wavelength regions among the fluorescence beams generated from the microparticle P can be separated and individually detected by one detector 7.

Furthermore, during the switching of the frequency f of the acoustic wave applied to the acousto-optic modulator 8 by the frequency controller 6, fluorescence detection by the detector 7 is not carried out. In addition, the fluorescence detection is carried out after delaying the fluorescence detection time by the detector 7 by the time until stabilization of the diffraction grating in the acousto-optic modulator 8 after the switching of the acoustic wave applied to the acousto-optic modulator 8. This makes it possible to detect fluorescence in the respective wavelength regions based on actual time.

Figure 5A:
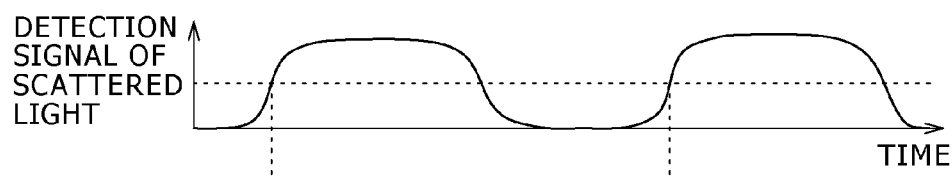
FIGS. 5A to 5D are chart diagrams for explaining the timings of switching of the frequency f by the frequency controller and the timings of the fluorescence detection time by the detector.
Figure 5B:
Figure 5C:
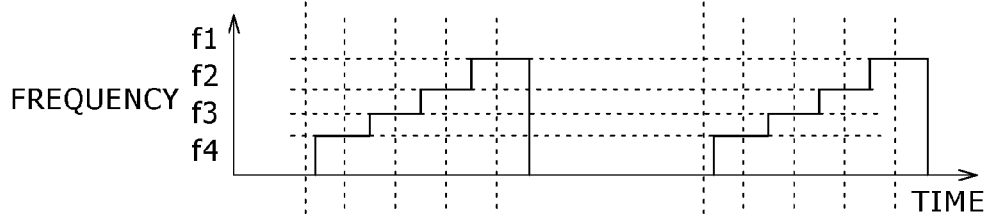
Figure 5D:
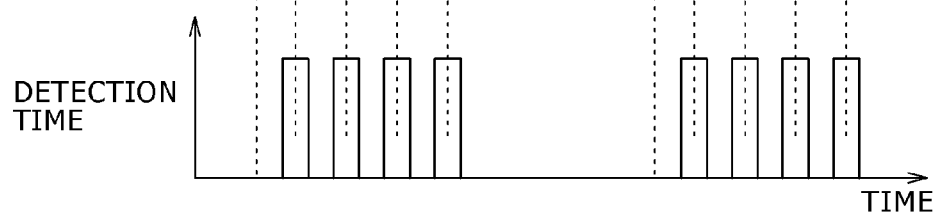
Figure 6:
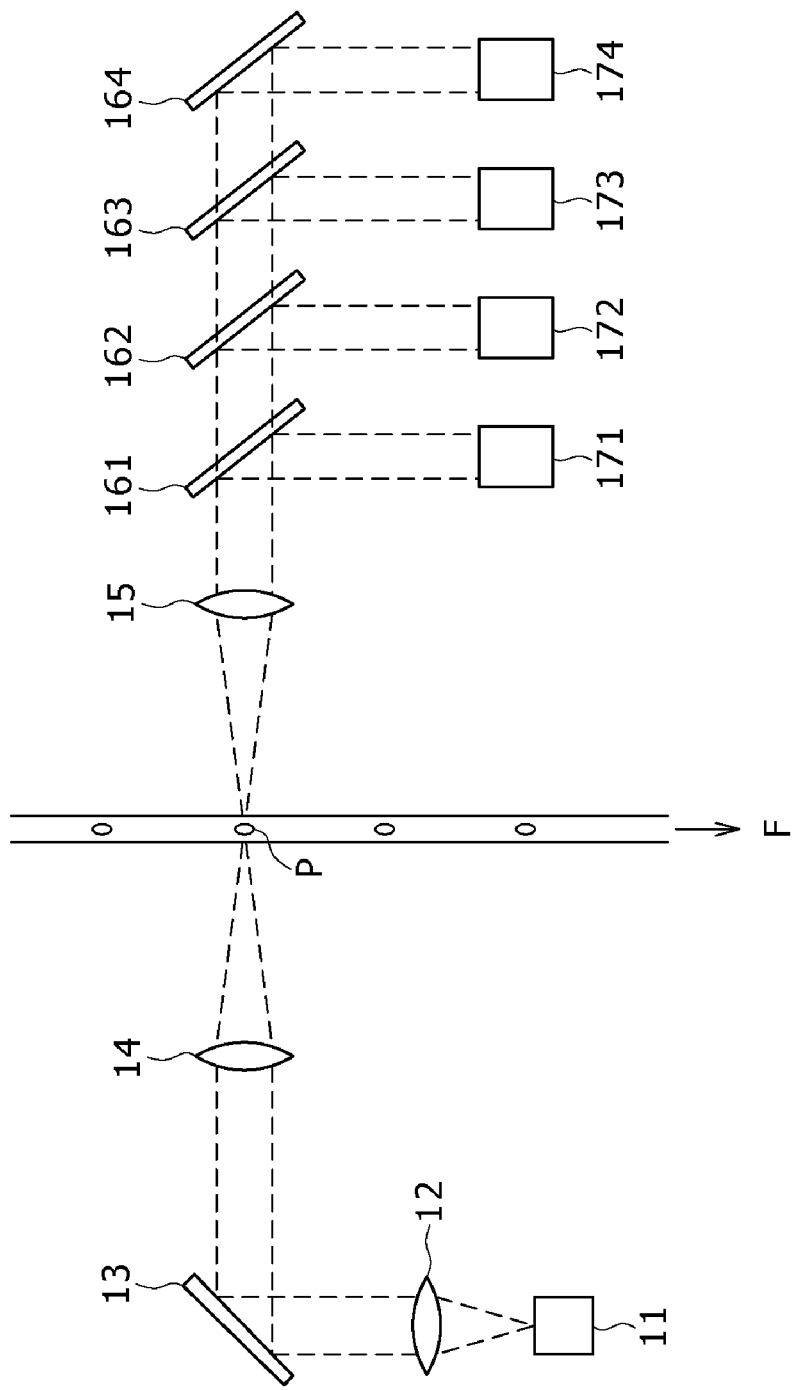
FIG. 6 is a schematic diagram for explaining an optical path for fluorescence detection in a microparticle analysis device of a related art.
Figure 7:
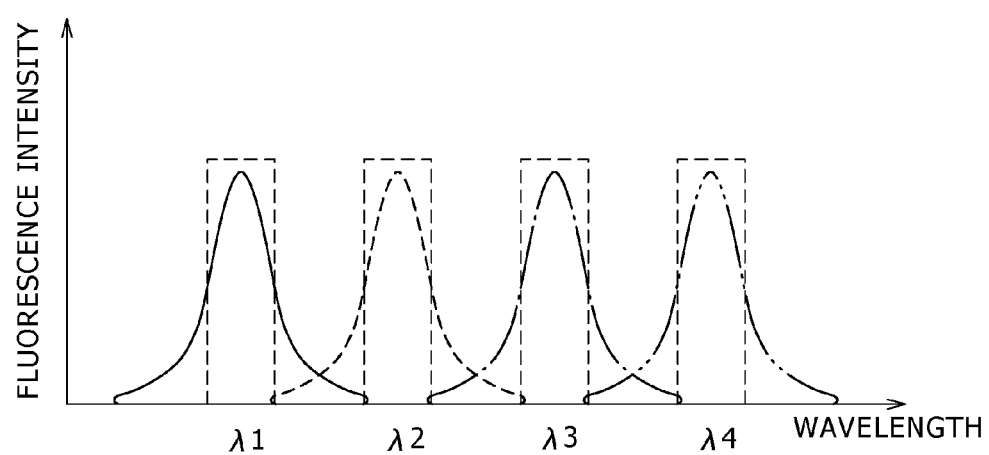
FIG. 7 is a schematic diagram for explaining the wavelength regions of fluorescence detected by each of plural detectors provided in the microparticle analysis device of the related art.

With reference to FIGS. 5A to 5D, the control method of the frequency controller 6 and the detector 7 in the microparticle analysis device according to the embodiment will be described below. FIG. 5A shows a detection signal from the detector to detect scattered light from microparticles. FIG. 5B shows a trigger signal output to the frequency controller 6 and the detector 7. FIG. 5C shows the frequency f of the acoustic wave applied to the acousto-optic modulator 8 by the frequency controller 6. FIG. 5D shows the fluorescence detection time by the detector 7.

Upon the passage of the microparticle P flowing in a flow cell or a flow path formed on a microchip through the light irradiation spot from the light source 1, scattered light from the microparticle P is detected by the detector for detecting scattered light. The detection signal of this scattered light (see FIG. 5A) is output to an overall controller during the passage of the microparticles P through the light irradiation spot from the light source 1. The detected scattered light may be e.g. forward-scattered light, side-scattered light, Rayleigh-scattered light, or Mie-scattered light.

The overall controller receives the output of this detection signal of the scattered light and outputs the trigger signal (see FIG. 5B) to the frequency controller 6 and the detector 7.

The frequency controller 6 receives the output of this trigger signal and discontinuously changes the frequency f of the acoustic wave applied to the acousto-optic modulator 8 to start switching of the detected-fluorescence wavelength region. Simultaneously, the detector 7 that has received the output of the trigger signal starts detection of fluorescence in the respective detected-fluorescence wavelength regions after the switching. At this time, the detector 7 carries out the detection of fluorescence in the respective detected-fluorescence wavelength regions with the intermediary of delaying by a predetermined time until stabilization of the diffraction grating in the acousto-optic modulator 8 after the switching of the frequency f by the acousto-optic modulator 8.

In this manner, during the passage of the microparticles P through the light irradiation spot from the light source 1, the frequency f of the acoustic wave applied to the acousto-optic modulator 8 by the frequency controller 6 is discontinuously changed. Thereby, fluorescence generated from the microparticles P is detected with high-speed switching of the detected-fluorescence wavelength region. This makes it possible to surely acquire the fluorescent characteristics of plural wavelength regions regarding the respective microparticles P with high efficiency. Although the example in which the frequency f is changed to four stages is shown in the diagram, the number of times of switching of the frequency f is not particularly limited.

Furthermore, during the switching of the frequency f of the acoustic wave applied to the acousto-optic modulator 8 by the frequency controller 6, the fluorescence detection by the detector 7 is not carried out. In addition, the start time of the fluorescence detection by the detector 7 is delayed by the time until stabilization of the diffraction grating in the acousto-optic modulator 8. This makes it possible to detect the fluorescence of the respective wavelength regions based on actual time and measure the fluorescent characteristics of the microparticles P with high accuracy.

In the above-described example, the frequency f of the acoustic wave applied to the acousto-optic modulator 8 by the frequency controller 6 is discontinuously switched in synchronization with the passage of the microparticles P through the light irradiation spot from the light source 1. However, of course it is also possible that the frequency f of the acoustic wave applied to the acousto-optic modulator 8 by the frequency controller 6 is always switched at high speed without synchronization with the microparticles P in the microparticle analysis device according to the embodiment.

Examples of specific numerical values of the respective configurations of the microparticle analysis device according to the embodiment will be shown below.

If $TeO_2$ is used as the crystal in the acousto-optic modulator 8 and the acoustic wave velocity v and the diffraction angle θ of the light of the diffraction center wavelength are set to 4260 m/s and 63 mrad, respectively, the diffraction center wavelength λ is 600 nm (see FIG. 2) when the frequency f of the acoustic wave applied to the acousto-optic modulator 8 is 450 MHz.

If a fluorescence beam with a diameter of 2 mm is incident on the crystal and the diffracted light is condensed by the condenser lens 52 having a focal length of 25 mm, 106 μm is figured out as the aperture width w of the slit 9 providing 40 nm as the wavelength width $\Delta\lambda_1$. The switching time of the diffraction center wavelength at this time is 0.47 μsec.

The microparticle analysis device according to the embodiment discontinuously changes the frequency of the acoustic wave applied to the acousto-optic modulator depending on the arbitrary detected-fluorescence wavelength region as the detection target, and thereby can separate fluorescence in plural wavelength regions among fluorescence beams generated from microparticles and individually detect the separated fluorescence by one detector. Therefore, in the microparticle analysis device according to the embodiment, plural detectors do not need to be provided, and the numbers of filters, mirrors, and so forth can also be greatly decreased to permit device size miniaturization. Furthermore, through the use of the acousto-optic modulator, which is a general-purpose device having high responsiveness, suppression of the device manufacturing cost is also permitted.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A microparticle analysis device comprising:
   a light source configured to irradiate a microparticle with light;
   an acousto-optic modulator configured to diffract fluorescence generated from the microparticle due to the light irradiation;
   a slit configured to allow transmission of only diffracted light in a diffraction center wavelength region among diffracted light beams from the acousto-optic modulator;
   a detector configured to detect the diffracted light in the diffraction center wavelength region transmitted through the slit;
   a controller configured to apply an acoustic wave to the acousto-optic modulator and discontinuously switch frequency of the acoustic wave; and
   a detector configured to detect scattered light generated from the microparticle due to the light irradiation, wherein
   the controller discontinuously switches the frequency of the acoustic wave applied to the acousto-optic modulator based on input of a detection signal from the detector to detect the scattered light.

2. A microparticle analysis method comprising:

diffracting fluorescence generated from a microparticle due to light irradiation by an acousto-optic modulator that provides a diffraction center wavelength region made to correspond with a detected-fluorescence wavelength region;

making diffracted light from the acousto-optic modulator be transmitted through a slit that allows transmission of only diffracted light in the diffraction center wavelength region;

detecting the diffracted light in the diffraction center wavelength region transmitted through the slit; and discontinuously switching frequency of an acoustic wave applied to the acousto-optic modulator, and wherein the frequency of the acoustic wave applied to the acousto-optic modulator is discontinuously switched during detection of scattered light generated from the microparticle due to the light irradiation.

* * * * *